US00PP26310P3

(12) United States Plant Patent
Meilland

(10) Patent No.: US PP26,310 P3
(45) Date of Patent: Jan. 19, 2016

(54) CREEPING ROSE PLANT NAMED 'MEIMEIGEA'

(50) Latin Name: *Rosa hybrida*
Varietal Denomination: Meimeigea

(71) Applicant: CP DELAWARE, INC., Wilmington, DE (US)

(72) Inventor: Alain A. Meilland, Antibes (FR)

(73) Assignee: CP DELAWARE, INC., Wilmington, DE (US)

( * ) Notice: Subject to any disclaimer, the term of this patent is extended or adjusted under 35 U.S.C. 154(b) by 239 days.

(21) Appl. No.: 13/998,689

(22) Filed: Nov. 25, 2013

(65) Prior Publication Data

US 2015/0150165 P1 May 28, 2015

(51) Int. Cl.
*A01H 5/02* (2006.01)

(52) U.S. Cl.
USPC ..... Plt./110

(58) Field of Classification Search
USPC ..... Plt./101, 109, 110
See application file for complete search history.

*Primary Examiner* — Susan McCormick Ewoldt
*Assistant Examiner* — Karen Redden
(74) *Attorney, Agent, or Firm* — Buchanan, Ingersoll & Rooney PC

(57) ABSTRACT

A new and distinct rose plant is provided that commonly commences blooming early in the season and forms abundantly and substantially continuously attractive substantially white semi-double blossoms which display no fragrance. The growth habit is low regular creeping and strong vegetation is formed. The vegetation is dense dark green and bears a matte aspect on the upper surface. Good disease tolerance is exhibited particularly with respect to Black Spot and Oidium. The plant is particularly well suited for providing attractive ornamentation in parks and gardens.

1 Drawing Sheet

Figures 1, 2, 3, 4, 5, 6, 7, 8, 9, 10, 11, 12, 13, 14, 15, 16, 17:
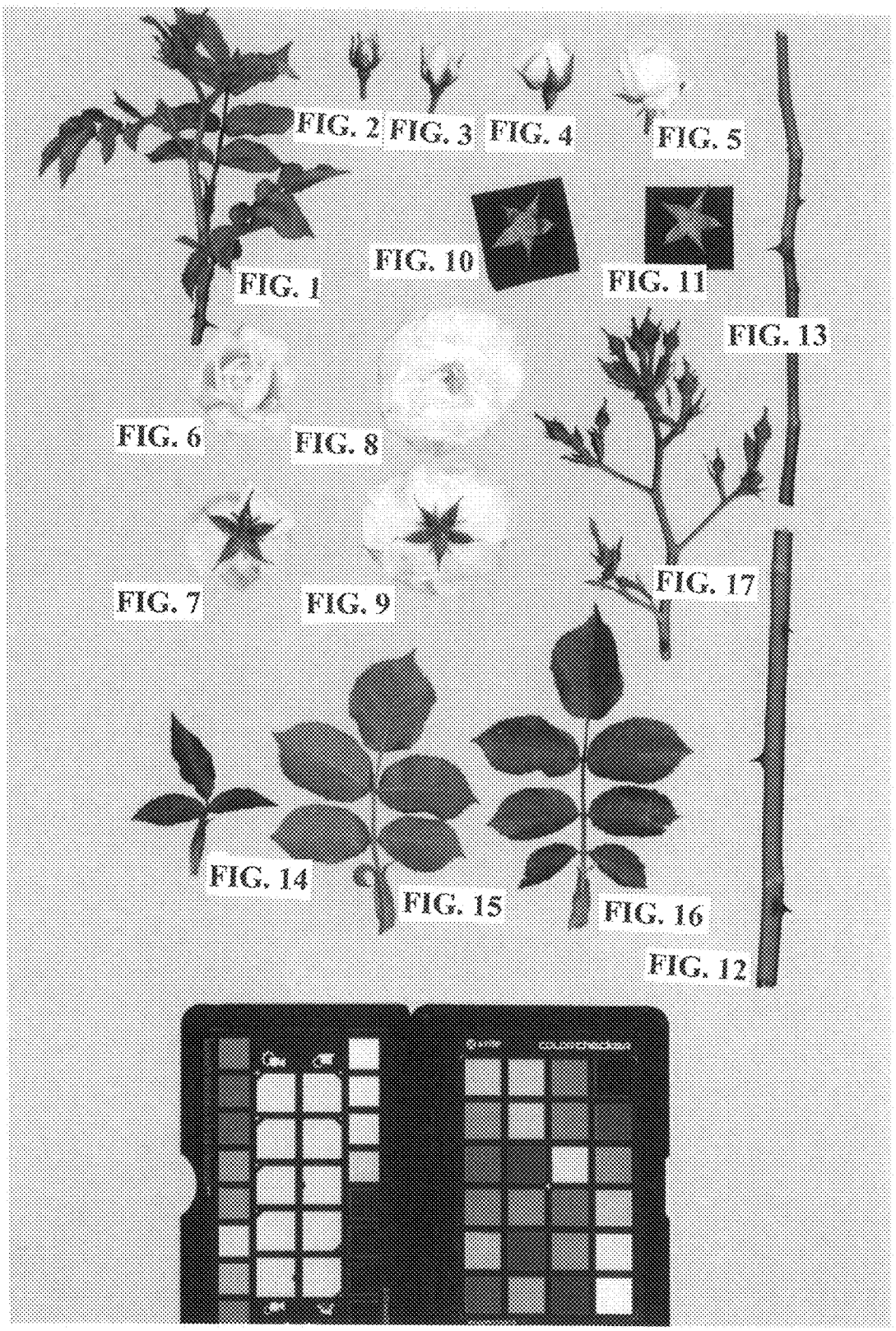

Botanical/commercial classification: *Rosa hybrida*/Creeping Rose Plant.

Varietal denomination: cv. Meimeigea.

SUMMARY OF THE INVENTION

The new variety of *Rosa hybrida* creeping rose plant was created by artificial pollination wherein two parents were crossed which previously had been studied in the hope that they would contribute the desired characteristics. The female parent (i.e., the seed parent) was the product of the cross of the 'Meijeunom' variety (U.S. Plant Pat. No. 19,143) and 'Meiglise' variety (U.S. Plant Pat. No. 15,960). The male parent (i.e., the pollen parent) was the 'Meibalneo' variety (non-patented).

The parentage of the new variety can be summarized as follows:

('Meijeunom'×'Meiglise')×'Meibalneo'.

The seeds resulting from the above pollination were sown and small plants were obtained which were physically and biologically different from each other. Selective study resulted in the identification of a single plant of the new variety.

It was found that the new rose plant of the present invention:

(a) displays a low regular creeping growth habit with strong vegetation,
(b) forms in abundance on a substantially continuous basis attractive substantially white semi-double blossoms,
(c) exhibits attractive dense dark green foliage with a matte aspect,
(d) exhibits good disease tolerance particularly with respect to Black Spot and Oidium, and
(e) is particularly well suited for providing attractive ornamentation in parks and gardens.

The blooming tends to commence early in the season, during observations to date.

The new variety well meets the needs of the horticultural industry and can be grown to advantage where attractive ornamentation is to be provided.

The new variety can be readily distinguished from its ancestors. For instance, the 'Meijeunom' variety forms fragrant ivory-white blossoms having a greater number of petals. The 'Meiglise' variety displays fragrant bright white blossoms having a lesser number of petals. The 'Meibalneo' variety displays dissimilar yellow blossoms.

The new variety also can be readily distinguished from the 'Meiviowit' variety (U.S. Plant Pat. No. 16,739), and the 'Meiguimov' variety (U.S. Plant Pat. No. 18,990) through an inspection of the blossoms. More specifically, the 'Meiviowit' variety forms dissimilar large very double blossoms, and the 'Meiguimov' variety forms dissimilar single pink blossom.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meimeigea'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during June while growing outdoors on their own roots at Le Cannet des Maures, Var, France. Comparative color information is included at the bottom.

FIG. 1—illustrates a specimen of a young shoot;

FIG. 2—illustrates a specimen of a floral bud at the opening of the sepals;

FIG. 3—illustrates a specimen of a floral bud wherein the sepals are more fully open;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a main branch;

FIG. 13—illustrates a specimen of a flowering stem;

FIG. 14—illustrates a specimen of a leaf with three leaflets—plan View—upper surface;

FIG. 15—illustrates a specimen of a leaf with five leaflets—plan view—upper surface;

FIG. 16—illustrates a specimen of a leaf with seven leaflets—plan View—upper surface; and FIG. 17—illustrates a cluster of buds.

DETAILED BOTANICAL DESCRIPTION

The chart used in the identification of the colors is that of The Royal Horticultural Society (R.H.S. Colour Chart—1995). The description is based on the observation of one-year-old plants during October which were growing outdoors on their own roots at Le Cannet des Maures, Var, France.

Class: Creeping.

Plant:

*Growth habit*.—Creeping.

*Height*.—Commonly appropriately 60 cm on average.

*Width*.—Commonly approximately 1 m on average.

Branches:

*Stem length*.—Commonly approximately 50 to 60 cm on average.

*Stem diameter*.—Commonly approximately 8 mm on average.

*Color*.—Young stems: near Yellow-Green Group 146B. Adult wood: near Yellow-Green Group 146B.

*Thorns*.—On young stems: Configuration: with an ovate base. Quantity: approximately 5 on average on a stem length of 10 cm. Length: approximately 0.7 cm on average. Color: near Greyed-Purple Group 184B. On adult stems: Configuration: rather upright on the upper surface and slightly concave on the under surface and with an ovate base. Quantity: approximately 10 on average on a stem length of 10 cm. Length: approximately 0.9 to 1 cm on average. Color: near Greyed-Orange Group 164B.

Leaves:

*Length*.—Commonly approximately 9 to 10 cm on average for a seven-leaflet leaf.

*Width*.—Commonly approximately 5.5 to 6 cm on average for a seven-leaflet leaf.

*Stipules*.—Adnate, pectinate, rather broad, approximately 1.1 cm in length on average, approximately 0.3 cm in width on average, near Green Group 137B on the upper surface, and near Green Group 138B on the under surface.

*Petioles*.—Upper surface: near Green Group 137A in coloration. Under surface: near Green Group 138A in coloration. Length: approximately 2.5 cm on average for the terminal leaflet. Texture: non-glandular on the upper surface, and with a few small prickles on the under surface.

*Rachis*.—Upper surface: near Green Group 137A in coloration. Under surface: near Green Group 138B in coloration. Texture: somewhat rough.

*Leaflets*.—Number: 3, 5 and 7 (most often). Shape: generally oval with an acuminate tip and an obtuse base. Size: the terminal leaflets commonly are approximately 3 cm in length on average and approximately 1.5 cm in width on average for a three-leaflet leaf, approximately 3 cm in length on average and approximately 1.5 cm in width for a five-leaflet leaf, and approximately 4 to 4.5 cm in length and approximately 2 to 2.5 cm in width for a seven-leaflet leaf. Serration: slightly denticulate. Texture: physically firm and leathery. Color (young foliage): Upper surface: near Green Group 137B. Under surface: near Green Group 138B. Color (adult foliage): Upper surface: near Green Group 137B. Under surface: near Green Group 138B. Venation: regular and alternately disposed from a main central vein.

Inflorescence:

*Number of flowers*.—Commonly approximately 5 to 12 blossoms per stem.

*Peduncle*.—Smooth, approximately 2.5 to 3 cm in length on average, approximately 0.1 cm in diameter on average, and near Yellow-Green Group 148B in coloration.

*Sepals*.—Upper surface: Tomentose and near Yellow-Green Group 148C to 148D in coloration. Under surface: smooth and near Yellow-Green Group 148B in coloration. Number: five. Shape: longish and upright at the base. Size: approximately 1.2 cm in length on average, and approximately 0.3 cm in width at the widest point on average.

*Buds*.—Shape: substantially conical. Size: small. Length: approximately 1 cm on average. Width: approximately 0.9 cm at the widest point on average. Color as calyx breaks: Upper surface: near Yellow Group 2C and 2D suffused with near Red Group 49D. Under surface: near Yellow Group 2C and 2D suffused with near Red Group 49D and Red Group 54A.

*Flower*.—Shape: cup-shaped. Diameter: approximately 4 to 5 cm on average. Color (in the course of opening): Upper surface: near Yellow Group 2C, amply suffused with near Red Group 49D, and with a spot of near Yellow Group 2C at the base. Under surface: on the internal petals near Yellow Group 2C and 2D suffused with near Red Group 49D, and on the external petals near Yellow Group 2C and 2D suffused with near Red Group 53D and near Red Group 54A, and with a spot of near Yellow Group 2C at the base. Color (open flower): Upper side: near White Group 155D with a spot of near Yellow Group 2C at the base. Under side: on the internal petals near White Group 155D, and on the external petals near White Group 155D more or less suffused with near Red Group 48D, and with a spot of near Yellow Group 2C at the base. Petal number: commonly between about 9 to 12 on average under normal growing conditions. Petal shape: with a substantially rounded tip and an obtuse base. Petal texture: smooth and somewhat flexible. Petal length: approximately 1.8 to 2.2 cm on average. Petal width: approximately 2.3 cm on average. Petal arrangement: imbricated, and without petaloids. Petal drop: good with the petals commonly detaching cleanly before drying. Fragrance: none detected. Stamen number: approximately 53 on average. Anthers: regularly arranged around the styles, approximately 0.2 cm in size on average, and near Yellow-Orange Group 15C in coloration. Filaments: approximately 0.2 cm in length on average, and near Yellow-Orange Group 16D in coloration. Pollen: none available for observation. Pistils: approximately 15 on average. Stigmas: approximately 0.1 cm in size on average, and near Yellow-Green Group 145D in coloration. Styles: approximately 0.1 cm in length on average, and near Yellow-Green Group 145D in coloration. Receptacle: smooth, funnel-shaped in longitudinal section, approximately 0.5 cm in length on average, approximately 0.4 cm in width on average at the widest point, and near Yellow-Green Group 148B in coloration. Hips: generally pitcher-shaped approximately 7 mm in length on average, approximately 6 mm in width on average at the widest point, and near Greyed-Orange Group 169A in coloration with the presence of seeds within.

Development:

*Vegetation*.—Strong.

*Blooming*.—Early season, very abundant and substantially continuous.

*Tolerance to diseases*.—Good particularly with respect to Black Spot (*Diplocarpon rosae*) and Oidium (*Podosphaera pannosa*).

The new 'Meimeigea' variety has not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following characteristics:

(a) displays a low regular creeping growth habit with strong vegetation, (b) forms in abundance on a substantially continuous basis attractive substantially white semi-double blossoms, (c) exhibits attractive dense dark green foliage with a matte aspect, (d) exhibits good disease tolerance particularly with respect to Black Spot and Oidium, and (e) is particularly well suited for providing attractive ornamentation in parks and gardens;

substantially as shown and described.

* * * * *